United States Patent
Cai et al.

(10) Patent No.: US 11,937,998 B2
(45) Date of Patent: Mar. 26, 2024

(54) HEARING PROTECTION DEVICE AND METHOD OF FORMING SAME

(71) Applicant: 3M INNOVATIVE PROPERTIES COMPANY, St. Paul, MN (US)

(72) Inventors: Feng Cai, Carmel, IN (US); Jeffrey L. Hamer, Springville, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 1398 days.

(21) Appl. No.: 16/088,474

(22) PCT Filed: Mar. 31, 2017

(86) PCT No.: PCT/US2017/025268
§ 371 (c)(1),
(2) Date: Sep. 26, 2018

(87) PCT Pub. No.: WO2017/173210
PCT Pub. Date: Oct. 5, 2017

(65) Prior Publication Data
US 2020/0297539 A1    Sep. 24, 2020

Related U.S. Application Data

(60) Provisional application No. 62/316,645, filed on Apr. 1, 2016.

(51) Int. Cl.
*A61F 11/08*    (2006.01)
*B65D 85/04*    (2006.01)
*H04R 1/10*    (2006.01)

(52) U.S. Cl.
CPC .............. *A61F 11/08* (2013.01); *B65D 85/04* (2013.01); *H04R 1/1033* (2013.01);
(Continued)

(58) Field of Classification Search
CPC . A61F 11/08; A61F 2250/0071; B65D 85/04; H04R 1/10; A61B 7/02; G02C 3/00
See application file for complete search history.

(56) References Cited

U.S. PATENT DOCUMENTS

| | | |
|---|---|---|
| 1,984,038 A | 12/1934 | Shaw |
| 2,704,961 A | 3/1955 | Weil |

(Continued)

FOREIGN PATENT DOCUMENTS

| | | |
|---|---|---|
| WO | WO 2004-039296 | 5/2004 |
| WO | WO 2015-020133 | 2/2015 |
| WO | WO 2015-179126 | 11/2015 |

OTHER PUBLICATIONS

International Search report for PCT International Application No. PCT/US2017/025268 dated Jun. 16, 2017, 4 pages.

*Primary Examiner* — Matthew W Schall
(74) *Attorney, Agent, or Firm* — Katherine M. Scholz

(57) ABSTRACT

Various embodiments of a hearing protection device and a method of forming such device are disclosed. The hearing protection device includes a first hearing protector, a second hearing protector, and an elongated connector including a first end that is connected to the first hearing protector and a second end that is connected to the second hearing protector. The device further includes a frangible attachment element disposed between a first portion of the elongated connector and a second portion of the elongated connector that temporarily connects the first portion to the second portion such that the elongated connector is in a compact configuration. The elongated connector is adapted to be disposed in an elongated configuration when the frangible attachment element is broken.

16 Claims, 5 Drawing Sheets

(52) U.S. Cl.
CPC . *A61F 2210/0071* (2013.01); *A61F 2220/005* (2013.01); *A61F 2250/0071* (2013.01)

(56) References Cited

U.S. PATENT DOCUMENTS

| | | |
|---|---|---|
| 4,193,396 A | 3/1980 | Wacker |
| 4,219,018 A | 8/1980 | Draper, Jr. |
| 4,253,452 A | 3/1981 | Powers |
| 4,314,553 A | 2/1982 | Wasterdal |
| 4,353,364 A | 10/1982 | Woods |
| 4,481,158 A | 11/1984 | Georlette |
| 4,555,313 A | 11/1985 | Duchane |
| 4,880,076 A | 11/1989 | Ahlberg |
| 4,896,679 A | 1/1990 | St.Pierre |
| 4,916,758 A | 4/1990 | Jordo-Ross |
| 5,074,375 A | 12/1991 | Grozil |
| 5,129,514 A | 7/1992 | Lilley, Jr. |
| 5,249,309 A | 10/1993 | Berg |
| 5,438,698 A | 8/1995 | Burton |
| 5,541,677 A | 7/1996 | Huhtala |
| 5,581,821 A | 12/1996 | Nakano |
| 5,668,354 A | 9/1997 | Falco |
| 5,711,313 A | 1/1998 | Fleming |
| 5,781,272 A | 7/1998 | Bright |
| 5,806,506 A | 9/1998 | Kitamura |
| 5,811,742 A | 9/1998 | Leight |
| 6,074,060 A | 6/2000 | Bruce |
| 6,340,227 B1 | 1/2002 | Solberg |
| 6,440,339 B1 | 8/2002 | Magidson |
| 6,568,395 B2 | 5/2003 | Tiemens |
| 6,902,029 B2 | 6/2005 | Weise |
| 6,938,622 B2 | 9/2005 | Huang |
| 7,013,491 B2 | 3/2006 | Ferrara |
| 7,192,136 B2 | 3/2007 | Howell |
| 7,314,047 B2 | 1/2008 | Falco |
| 7,348,490 B2 | 3/2008 | Sakai |
| 7,384,936 B2 | 6/2008 | Csakai |
| 7,402,754 B2 | 7/2008 | Kirwan, Jr. |
| 7,537,011 B2 | 5/2009 | Falco |
| 7,784,583 B1 | 8/2010 | Hall |
| 8,068,633 B2 | 11/2011 | Lee |
| 8,155,361 B2 | 4/2012 | Schindler |
| 8,503,711 B2 | 8/2013 | Flynn |
| 8,708,091 B2 | 4/2014 | Barwacz |
| 8,774,443 B1 | 7/2014 | Anderson |
| 8,783,531 B2 | 7/2014 | Kroupa |
| 8,848,966 B2 | 9/2014 | Alstad |
| 8,873,250 B2 | 10/2014 | Kroupa |
| 2002/0040945 A1 | 4/2002 | Stepancich |
| 2002/0124851 A1 | 9/2002 | Knauer |
| 2004/0079579 A1* | 4/2004 | Barwacz ............ A61F 11/08 181/135 |
| 2004/0139976 A1 | 7/2004 | Taylor |
| 2005/0229938 A1 | 10/2005 | Jenkins |
| 2005/0230181 A1* | 10/2005 | Woo ............ A61F 11/12 181/135 |
| 2007/0086599 A1 | 4/2007 | Wilmink |
| 2007/0227546 A1 | 10/2007 | Schmaier |
| 2007/0284182 A1 | 12/2007 | Mu |
| 2009/0165189 A1 | 7/2009 | Purcell |
| 2009/0199326 A1 | 8/2009 | Brauner |
| 2009/0314515 A1* | 12/2009 | Bevirt ............ H01B 7/40 174/110 R |
| 2011/0162883 A1 | 7/2011 | Groset |
| 2012/0073583 A1 | 3/2012 | Turdjian |
| 2012/0121120 A1 | 5/2012 | Gorzelany |
| 2012/0159903 A1 | 6/2012 | Cooper |
| 2012/0272974 A1 | 11/2012 | Magidson |
| 2013/0014768 A1 | 1/2013 | Vaarbroe |
| 2013/0020425 A1 | 1/2013 | Grassi |
| 2013/0298356 A1 | 11/2013 | Scandora |
| 2014/0196727 A1 | 7/2014 | Barwacz |

* cited by examiner

HEARING PROTECTION DEVICE AND METHOD OF FORMING SAME

BACKGROUND

Hearing protection is widely used in industry and by consumers to protect a wearer from noise. Various types of hearing protection devices are available. For example, hearing protection devices can include over-the-ear configurations such as ear muffs and in-ear configurations such as earplugs. An in-ear hearing protection device can include first and second hearing protectors that are connected together by a flexible cord or connector to prevent loss of the hearing protectors during usage or to conveniently drape the hearing protectors around the neck, or to attach to a collar or helmet when the hearing protector is not in use. The flexible connector typically has a fixed length of between 21-27 inches.

Several types of earplugs are known. For example, roll-down type earplugs typically have a resilient foam body that is compressed by a user to reduce a diameter thereof. A portion of the reduced diameter earplug body is then inserted into the ear canal and allowed to slowly expand therein to fill the canal and provide desired attenuation. The remaining portion of the earplug body extends from the ear canal and provides a handle for removing the plug. Further, for example, a push-to-fit earplug includes a resilient body having a rigid or semi-rigid stem embedded therein and, most typically, extending therefrom. The stem provides a degree of rigidity to the earplug that facilitates insertion of the plug body into the ear canal. During use, the exposed stem portion of the push-in stem earplug extends from the ear canal, thus providing a handle for removal of the earplug.

SUMMARY

In general, the present disclosure provides various embodiments of a hearing protection device and a method of forming such device. The hearing protection device can include a first hearing protector, a second hearing protector, and an elongated connector that includes a first end that is connected to the first hearing protector and a second end that is connected to the second hearing protector. The hearing protection device can also include an attachment element disposed between a first portion of the elongated connector and a second portion of the elongated connector that temporarily connects the first portion to the second portion such that the elongated connector is in a compact configuration. In one or more embodiments, the elongated connector is adapted to be disposed in an elongated configuration when the attachment element is broken or separated.

In one aspect, the present disclosure provides a hearing protection device that includes a first hearing protector, a second hearing protector, and an elongated connector including a first end that is connected to the first hearing protector and a second end that is connected to the second hearing protector. The device further includes a frangible attachment element disposed between a first portion of the elongated connector and a second portion of the elongated connector that temporarily connects the first portion to the second portion such that the elongated connector is in a compact configuration. The elongated connector is adapted to be disposed in an elongated configuration when the frangible attachment element is broken.

In another aspect, the present disclosure provides a method that includes forming an elongated connector including a first end and a second end, and connecting a first hearing protector to the first end of the elongated connector and a second hearing protector to the second end of the elongated connector. The method further includes disposing a frangible attachment element between a first portion of the elongated connector and a second portion of the elongated connector, and temporarily connecting the first portion of the elongated connector to the second portion of the elongated connector with the frangible attachment element such that the elongated connector is in a compact configuration.

In another aspect, the present disclosure provides a hearing protection system that includes a plurality of hearing protectors, and an elongated connector including a first end that is adapted to connect to a first hearing protector of the plurality of hearing protectors and a second end that is adapted to connect to a second hearing protector of the plurality of hearing protectors. The system further includes a frangible attachment element disposed between a first portion of the elongated connector and a second portion of the elongated connector that temporarily connects the first portion to the second portion such that the elongated connector is in a compact configuration. The elongated connector is adapted to be disposed in an elongated configuration when the frangible attachment element is broken.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
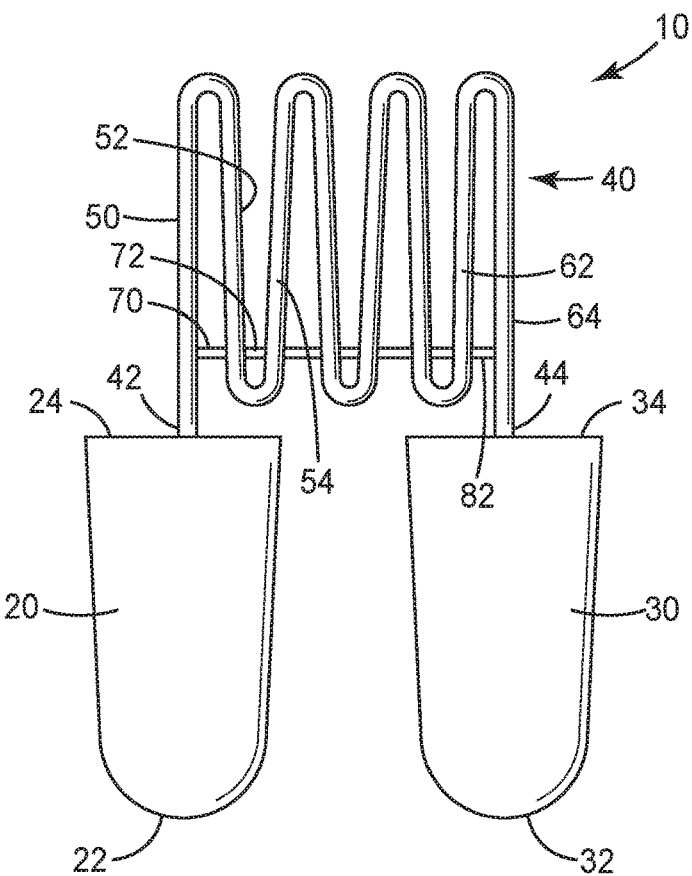
FIG. 1 is a schematic plan view of one embodiment of a hearing protection device in a compact configuration.

In general, the present disclosure provides various embodiments of a hearing protection device and a method of forming such device. The hearing protection device can include a first hearing protector, a second hearing protector, and an elongated connector that includes a first end that is connected to the first hearing protector and a second end that is connected to the second hearing protector. The hearing protection device can also include an attachment element disposed between a first portion of the elongated connector and a second portion of the elongated connector that temporarily connects the first portion to the second portion such that the elongated connector is in a compact configuration. In one or more embodiments, the elongated connector is adapted to be disposed in an elongated configuration when the attachment element is broken or separated.

Packaging a hearing protection device can be challenging as the elongated connector may need to be coiled or bundled such that the device can be packaged in as small a package as is permissible. Various techniques have been utilized to bundle these types of hearing protection devices. For example, during packaging, a clip can be attached to a wound connector to form a circular-shaped bundle. The clip can retain the connector in this wound configuration. Further, during packaging, such clip can keep the connector wound to maintain compactness of the hearing protection device and to prevent the connector from unwinding during packaging. The more compact the wound connector, the less packaging material required. Compactness of the connector bundle during packaging is also advantageous in facilitating insertion of the bundle into the package.

Such clips, however, are separate products that require an additional step for applying the clip to the wound connector. Further, the clip can occupy space within the packaging, thereby requiring the use of larger packages. And a user must remove the clip prior to donning the hearing protection device.

One or more embodiments of hearing protection devices of the present disclosure can simplify the manufacturing and packaging processes required to package such devices individually. Further, one or more of these embodiments can reduce the size of the packaging required as the connector can remain wound in a desired compact configuration both during the packaging process and after the device been packaged. Such wound connectors can provide a reduced profile such that the connectors can be easier to store and transport. In addition, the wound connector can reduce the complexity of packaging equipment required to form a knot in a connector of the protection device or apply a clip or paper sleeve to the connector such that the connector remains wound. In one or more embodiments, the hearing protection device can be formed using a molding process where one or more hearing protectors of the device can be molded to a connector within the same mold, thereby reducing one or more steps of forming the hearing protection device. A user can unwind or separate the connector of the hearing protection device by applying a minimal separation force to the connector, e.g., by grasping the connector adjacent its first and second ends and pulling such ends away from each other such that the connector is in an elongated configuration.

Figure 2:
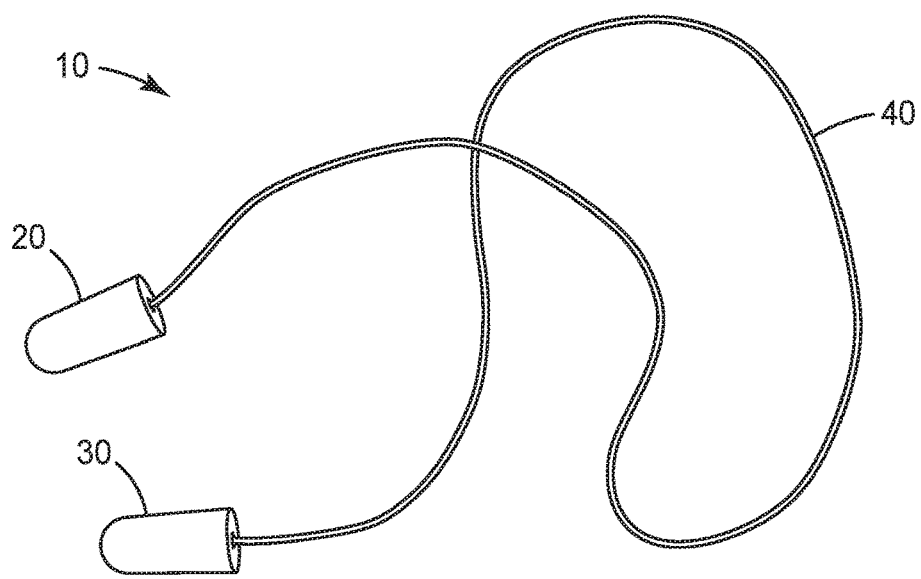
FIG. 2 is a schematic plan view of the hearing protection device of FIG. 1 in an elongated configuration.
Figure 3:
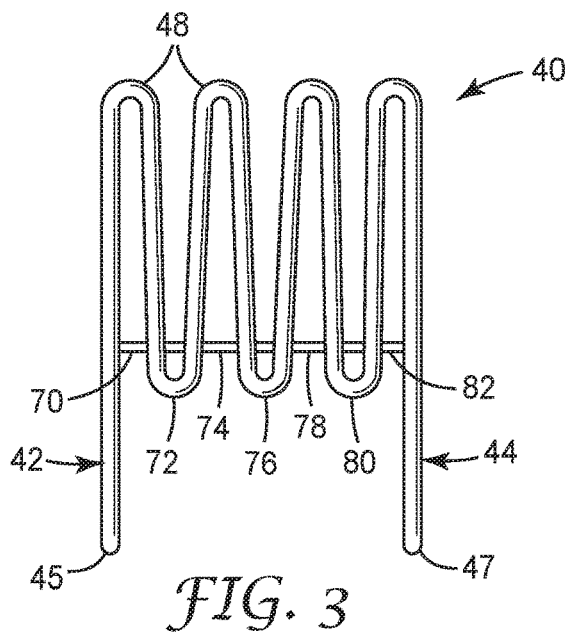
FIG. 3 is a schematic plan view of an elongated connector of the hearing protection device of FIG. 1.

FIGS. 1-3 are various views of one embodiment of a hearing protection device 10. The device 10 includes a first hearing protector 20, a second hearing protector 30, and an elongated connector 40. The elongated connector 40 can connect the first hearing protector 20 to the second hearing protector 30. Further, the elongated connector 40 can include a first end 42 and a second end 44. In one or more embodiments, a first portion 50 of the connector 40 can be connected or attached to a second portion 52 of the connector. In one or more embodiments, the first portion 50 can be temporarily connected to the second portion 52.

The device 10 also includes an attachment element 70 disposed between the first portion 50 of the elongated connector 40 and the second portion 52 of the elongated connector. In one or more embodiments, the attachment element 70 can be a frangible attachment element, i.e., an attachment element that can be broken or separated such that the portions connected together by the attachment element are permanently separated. The frangible attachment element 70 is a one-use element that cannot be used to reconnect the first and second portions 50, 52 once these portions have become separated. In one or more embodiments, the attachment element 70 temporarily connects the first portion 50 to the second portion 52 such that the elongated connector 40 is in a compact configuration as shown in FIG. 1. When the attachment element 70 becomes broken or separated, the elongated connector 40 is adapted to be disposed in an elongated configuration as shown in FIG. 2. The first portion 50 can be temporarily connected to any suitable number of portions of the elongated connector 40. For example, in one or more embodiments, the first portion 50 can be temporarily connected to the second portion 52 and one or more additional portions of the elongated connector 40 using any suitable technique or combination of techniques. In one or more embodiments, the device 40 can include an additional attachment element (not shown) disposed between the first portion 50 of the elongated connector 40 and an additional portion of the elongated connector that temporarily connects the first portion to the additional portion. The elongated connector 40 is adapted to be disposed in an elongated configuration when the attachment element 70 and the additional attachment element are broken.

The first and second hearing protectors 20, 30 can include any suitable hearing protector. In one or more embodiments, one or both of the first and second hearing protectors 20, 30 include earplugs as illustrated in FIGS. 1-3. Each of the hearing protectors 20, 30 can include any suitable type of earplug, e.g., roll-down type resilient foam earplugs, push-and-stem type earplugs, premolded polymeric flanged type earplugs, etc. The hearing protectors 20, 30 can include any suitable material or combination materials and take any suitable shape or combination of shapes. In one or more embodiments, one or both of the first and second hearing protectors 20, 30 can include a premolded body of a resilient polymeric material, e.g., foam. In such embodiments, the premolded body can include a stem portion and a plurality of radially extending flanged elements disposed on the stem portion as described, e.g., in U.S. Pat. Nos. 7,314,047 and 7,537,011 to Falco. These flanged elements can include substantially circular cross-sections and extend from the stem portion in a direction toward a rear of the stem portion to form an annular space between the flanges and the stem portion.

In one or more embodiments, one or both of the first and second hearing protectors 20, 30 can include a foam material that is resilient such that a user may insert the hearing protectors into the user's ear canals. The first hearing protector 20 includes a first end 22 and a second end 24, and the second hearing protector 30 includes a first end 32 and a second end 34. Each of the first ends 22, 32 of the first and second hearing protectors 20, 30 is adapted to be inserted into an ear canal of a user. Further, the second ends 24, 34 can be adapted to be connected to the elongated connector 40. For example, the second end 24 of hearing protector 20 is connected to the first end 42 of the elongated connector 40, and the second end 34 of the second hearing protector 30 is connected to the second end 44 of the elongated connector. In one or more embodiments, the second ends 24, 34 can also provide an engagement portion or handle for adjusting and removing the hearing protectors 20, 30. In one or more embodiments, one or both of the first and second hearing protectors 20, 30 can include a foam element fixed to a stem, where the stem extends from the foam element. In such embodiments, the elongated connector 40 can be attached to the stem of the respective hearing protector 20, 30.

The first and second hearing protectors 20, 30 can be connected by the elongated connector 40. The elongated connector 40 can include any suitable material or combination materials, e.g., metal, polymer, natural fiber such as cotton, etc. In one or more embodiments, the elongated connector 40 can include a rubber material. Further, in one or more embodiments, the elongated connector 40 can include any suitable polymeric material or combination of polymeric materials, e.g., thermoplastic materials, thermoplastic elastomers, polyurethanes, ethylene-vinyl acetates, styrene block copolymers, low-density polyethylenes, thermoplastic polyolefins, polyethylene terephthalates, and combinations and copolymers thereof. The elongated connector 40 can include a core that includes a polymeric material and a sheath that includes any suitable material or combination materials. In one or more embodiments, the elongated connector 40 can include a flexible polymeric material. In one or more embodiments, the elongated connector 40 can include a stretchable polymeric material, a stretchable shape memory polymeric material, etc. Further, the elongated connector 40 can have a solid cross-section or one or more portions of the connector can be hollow.

The elongated connector 40 can take any suitable cross-sectional shape and have any suitable dimensions. In one or more embodiments, the elongated connector 40 can have a circular cross-sectional shape. In one or more embodiments, a cross-sectional area of the elongated connector 40 can be substantially the same along a length of the connector between the first and second ends 42, 44. In one or more embodiments, the elongated connector 40 can have a cross-sectional area that varies in one or more portions along the length of connector. Further, the elongated connector 40 can have any suitable length, e.g., at least about 5 inches and no greater than about 30 inches.

The first end 42 of the elongated connector 40 can be connected to the second end 24 of the first hearing protector 20, and the second end 44 of the connector can be connected to the second end 34 of the second hearing protector 30 using any suitable technique or combination of techniques, e.g., sonic welding, adhesive bonding, mechanical bonding, friction-fitting, etc. In one or more embodiments, one or both of the first and second hearing protectors 20, 30 can be connected to the elongated connector 40 by forming the first and second hearing protectors in a mold along with the elongated connector. In one or more embodiments, the elongated connector 40 can include a first coupler 45 adjacent the first end 42 and a second coupler 47 adjacent the second and 44 (FIG. 3). As used herein, the term "adjacent the first end" means that an element or component is disposed closer to the first end 42 of the elongated connector 40 than to the second end 44. Further, the term "adjacent the second end" means that an element or component is disposed closer to the second end 44 of the elongated connector 40 than to the first end 42. The first and second couplers 45, 47 can be adapted to attach the first and second hearing protectors 20, 30 to the connector 40. For example, in one or more embodiments, each of the first and second hearing protectors 20, 30 can include an opening or slot that is adapted to receive the respective first and second coupler 45, 47. In such embodiments, the first and second hearing protectors 20, 30 can be retained on the first and second couplers 45, 47 using any suitable technique or combination of techniques, e.g., the first and second hearing protectors can be friction-fit onto the first and second couplers, adhered to the first and second couplers using any suitable adhesive, thermally bonded to the first and second couplers, etc.

As illustrated in FIG. 1, the elongated connector 40 includes two or more portions that are connected or attached together such that the elongated connector is in a compact configuration. Such portions can, in one or more embodiments, be temporarily connected. As used herein, the phrase "temporarily connected" means that one or more portions of the connector 40 are connected such that a separation force applied to such portions can permanently disconnect the portions without separating the connector into two or more segmented pieces. In other words, the first and second hearing protectors 20, 30 remain connected together by the elongated connector after these attached portions have been permanently disconnected. Once two portions of the elongated connector 40 that are temporarily connected have been separated, these two portions cannot be reconnected as the attachment element for connecting the two portions is either removed or rendered inoperable (e.g., broken). Any suitable number of portions of the elongated connector 40 can be connected together using any suitable number of attachment elements.

Any suitable technique or combination of techniques can be utilized to connect two or more portions of the elongated connector 40 together, e.g., adhering, chemical bonding, mechanically attaching, etc. As shown in FIG. 1, a first portion 50 of the elongated connector 40 is connected to a second portion 52 of the connector by a first attachment element 70. Further, the second portion 52 is connected to a third portion 54 by a second attachment element 72. Any suitable number of portions of the connector 40 can be connected together utilizing any suitable number of attachment elements. Although the hearing protection device 10 is illustrated as including 7 attachment elements, the device can include any suitable number of attachment elements. In the embodiment illustrated in FIGS. 1-3, the first and second attachment elements 70, 72 are lands that can be formed using any suitable technique or combination of techniques.

The first and second attachment elements 70, 72 can have any suitable dimensions and take any suitable shape such that the portions of the connector 40 that are connected by the elements can be separated without altering the integrity of the connector 40. Further, each of the first and second attachment elements 70, 72 can be disposed in any suitable location between two portions of the connector 40 such that the portions are connected together. The attachment elements 70, 72 can include any suitable material or combination of materials. In one or more embodiments, one or both of the first and second attachment elements 70, 72 can include the same material or materials as those of the connector 40. In one or more embodiments, one or more attachment elements can be integral with one or more portions of the elongated connector, i.e., material from the one or more portions of the connector can be utilized to form the one or more attachment elements. For example, in one or more embodiments, the first attachment element 70 can be integral with at least one of the first portion 50 and the second portion 52 of the elongated connector 40.

In one or more embodiments, the elongated connector 40 can be adapted such that the first and second portions 50, 52 of the connector can be permanently disconnected by applying a separation force to the connector 40 that breaks at least one or both of the first and second attachment elements 70, 72. The separation force can have any suitable value. In one or more embodiments, the separation force can be less than a tensile strength of the connector 40. When one or more of the attachment elements 70, 72 have been broken or separated, the elongated connector 40 is in an elongated configuration.

In one or more embodiments, two or more portions of the elongated connector 40 can be connected utilizing the same technique or combination of techniques. For example, as illustrated in FIG. 1, each of the connected portions of the elongated connector 40 are connected by an attachment element, e.g., attachment element 70. In one or more embodiments, the first and second portions 50, 52 can be connected using a technique or mechanism that is different from a technique used to connect the second and third portions 52, 54.

When one or more portions of the connector 40 are connected together, the elongated connector 40 can be considered to be in the compact configuration as illustrated in FIG. 1. When in the compact configuration, the elongated connector 40 can take any suitable shape or combination of shapes, e.g., coil, disk, rectangular, tubular, serpentine, etc. In one or more embodiments, the elongated connector 40 can include a coiled configuration. Such coiled configuration can be a two-dimensional coiled configuration or a three-dimensional (e.g., cylindrical) coiled configuration as is further described herein.

Once the two or more portions of the elongated connector 40 have been disconnected or detached, the elongated connector is in the elongated configuration and can take any suitable shape or combination of shapes. For example, FIG. 2 is a schematic plan view of the hearing protection device 10 of FIG. 1. As illustrated in FIG. 2, the portions of the elongated connector 40 that were connected when the elongated connector was in the compact configuration have become permanently disconnected. In one or more embodiments, two or more portions of the connector 40 can remain attached or connected even though the hearing protection device 10 has been donned by the user. In general, the user may desire that two or more portions of the connector remain connected while the hearing protection device 10 is in use, thereby allowing the user to tailor the length of the elongated connector 40 while wearing the device such that the connector remains at a length that is not as prone to becoming engaged with machinery or portions of clothing or headgear being worn by the user.

For example, in reference to FIG. 1, the user can disconnect the first and second portions 50, 52 of the connector 40 by applying a separation force to (e.g., pulling apart) these portions such that the first attachment element 70 is broken or separated. Further, the user may also disconnect additional portions 62, 64 of the connector 40 by applying a separation force to (e.g., pulling apart) such portions such that an additional attachment element 82 that temporarily connects these portions is broken or separated. The user may insert the first hearing protector 20 in one ear and the second hearing protector 30 in the other ear while leaving the second portion 52 of the connector 40 connected to the third portion 54, and any other additional connected portions connected together. In one or more embodiments, the user may apply a separation force to the elongated connector 40 such that all connected portions become permanently disconnected.

The connector 40 when in the compact configuration can be packaged within a smaller profile package along with the first and second hearing protectors 20, 30, and one or more additional hearing protectors. In one or more embodiments, the connector 40 can be packaged with a plurality of hearing protectors to provide a hearing protection system. In one or more embodiments, the hearing protectors 20, 30 can be connected to the elongated connector 40 when in the package. In one or more embodiments, the hearing protectors 20, 30 can be disconnected from the elongated connecter 40 when in the package, and the user can remove the connecter and hearing protectors from the package and attached the protectors to the connector using any suitable technique or combination of techniques either while the connector is in the compact configuration or after the connector has been manipulated to the elongated configuration.

As mentioned herein, the elongated connector 40 can take any suitable shape or combination of shapes when in the compact configuration. For example, FIG. 3 is a schematic plan view of the elongated connector 40 of the hearing protection device 10 of FIG. 1 with the first and second hearing protectors 20, 30, removed for clarity. As shown in FIG. 3, the elongated connector 40 is in a serpentine-shaped compact configuration. The serpentine-shaped compact configuration includes two or more curved portions 48 that can be held in place by attachment elements 70, 72, 74, 76, 78, 80, and 82. The two or more curved portions 48 can each have any suitable radius of curvature to provide a desired width or profile of the elongated connector when the connector is in the compact configuration.

Figure 4:
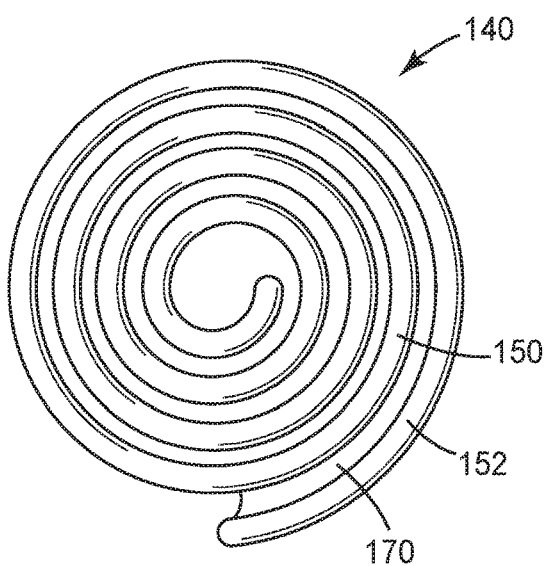
FIG. 4 is a schematic plan view of another embodiment of an elongated connector that can be utilized with the hearing protection device of FIG. 1.

Further, as mentioned herein, the elongated connector 40 can have a coiled shape when in the compact configuration. For example, FIG. 4 is a schematic plan view of another embodiment of an elongated connector 140. All of the design considerations and possibilities regarding the elongated connector 40 of FIGS. 1-3 apply equally to the elongated connector 140 of FIG. 4. The elongated connector 140 of FIG. 4 can be utilized with any suitable hearing protection device, e.g., hearing protection device 10 of FIGS. 1-3.

One difference between the elongated connector 140 of FIG. 4 and elongated connector 40 of FIGS. 1-3 is that the elongated connector 140 includes a coiled shape when the connector is in a compact configuration as shown in FIG. 4. Further, two or more portions of the elongated connector 140 can be connected by one or more attachment elements 170. For example, a first portion 150 of the connector 140 is connected to a second portion 152 of the connector 140 by the attachment element 170 that is a land disposed between the first and second portions. The land 170 can have any suitable dimensions and take any suitable shape. In one or more embodiments, the land 170 can be disposed along an entire length of the elongated connector 140. In one or more embodiments, the land 170 can include two or more portions that are separated by gaps and disposed along a portion or portions of the connector 140. This coiled shape of the elongated connector 140 can be a two-dimensional shape or a three-dimensional shape. As illustrated in FIG. 4, the coiled shape is a two-dimensional coiled shape, i.e., the connector 140 when in the compact configuration can substantially lie in a plane.

The connector 140 in the coiled configuration illustrated in FIG. 4 can be packaged within a smaller profile package along with two or more hearing protectors (e.g., hearing protectors 20, 30 of FIGS. 1-3). The hearing protectors can be connected to the elongated connector 140 when in the package. In one or more embodiments, the hearing protectors can be disconnected from the elongated connecter when in the package, and the user can remove the connecter and hearing protectors from the package and attach the protectors to the connector using any suitable technique or combination of techniques.

Figure 5:
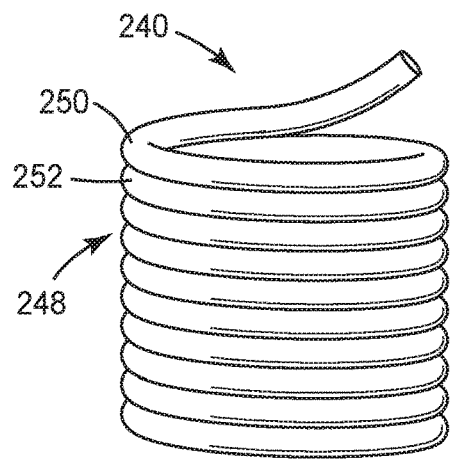
FIG. 5 is a schematic plan view of another embodiment of an elongated connector that can be utilized with the hearing protection device of FIG. 1.

FIG. 5 is a schematic perspective view of another embodiment of an elongated connector 240. All of the design considerations and possibilities regarding the elongated connector 40 of FIGS. 1-3 and the elongated connector 140 of FIG. 4 apply equally to the elongated connector 240 of FIG. 5.

One difference between the elongated connector 240 of FIG. 5 and elongated connector 40 of FIGS. 1-3 is that the elongated connector 240 takes a three-dimensional (e.g., cylindrical) coiled shape when in a compact configuration. The compact configuration can have any suitable cross-sectional shape, e.g., elliptical, triangular, rectilinear, etc. Two or more portions of the elongated connector 240 can be connected using any suitable technique or combination of techniques. The elongated connector 240 can be packaged with two or more hearing protectors (e.g., first and second hearing protectors 20, 30 of FIGS. 1-3) that are disconnected from the elongated connector 240. In one or more embodiments, two hearing protectors can be connected to the elongated connector 240 when the connector is in the coiled configuration and in a package.

As shown in FIG. 5, a first portion 250 of the elongated connector 240 can be connected to a second portion 252 of the connector using any suitable technique or combination of techniques. The first portion 250 can be temporarily connected to any suitable number of portions of the elongated connector 240. For example, in one or more embodiments, the first portion 250 can be connected to the second portion 252 and one or more additional portions. Further, the second portion 252 can be temporarily connected to the first portion 250 and one or more additional portions of the elongated connector.

Figure 6:
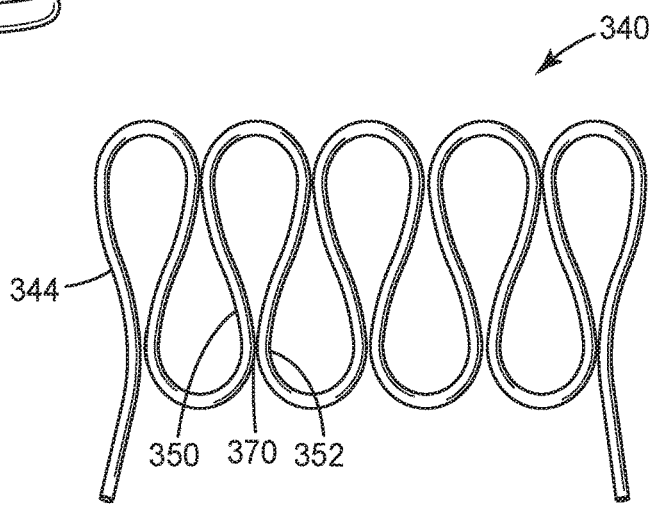
FIG. 6 is a schematic plan view of another embodiment of an elongated connector that can be utilized with the hearing protection device of FIG. 1.

FIG. 6 is a schematic plan view of another embodiment of an elongated connector 340. All of the design considerations and possibilities regarding the elongated connector 40 of FIGS. 1-3 and the elongated connector 140 of FIG. 4 apply equally to the elongated connector 340 of FIG. 6. The elongated connector 340 can take a serpentine shape when in a compact configuration that includes S-shaped portions that are connected together by one or more attachment elements 370. For example, a first portion 350 of the connector 340 is temporarily connected to a second portion 352 of the connector by attachment element 370. The compact configuration of the connector 340 can include any suitable number of S-shaped portions temporarily connected together by any suitable number of attachment elements.

Figure 9:
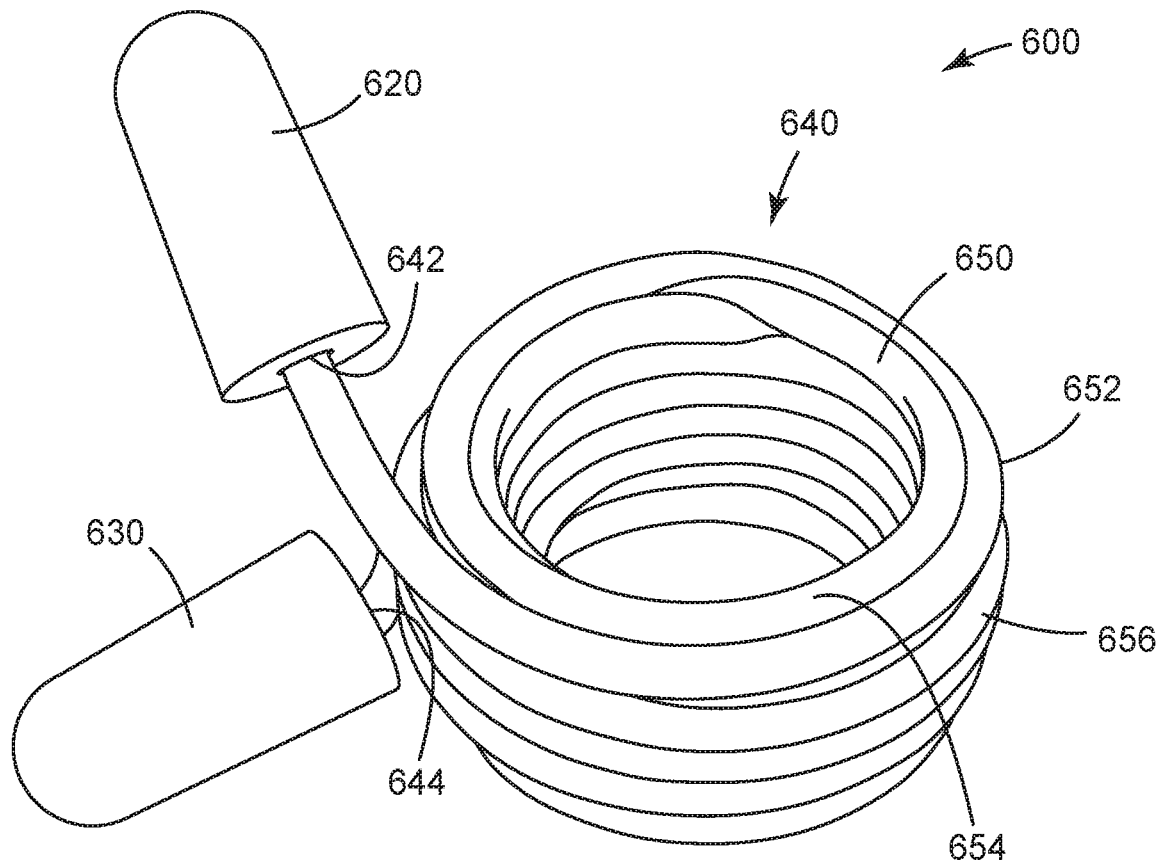
FIG. 9 is a schematic perspective view of another embodiment of a hearing protection device in a compact configuration.

As mentioned herein, each of the hearing protection devices described herein can include any elongated connector that can take any suitable shape when in a compact configuration. For example, FIG. 9 is a schematic perspective view of another embodiment of a hearing protection device 600. All of the design considerations and possibilities regarding the hearing protection device 10 of FIGS. 1-3 apply equally to the hearing protection device 600 of FIG. 9. The hearing protection device 600 includes a first hearing protector 620, a second hearing protector 630, and an elongated connector 640. The elongated connector 640 includes a first end 642 that is connected to the first hearing protector 620 and a second end 644 that is connected to the second hearing protector 630.

One difference between hearing protection device 600 of FIG. 9 and device 10 of FIGS. 1-3 is that the elongated connector 640 takes a coiled shape when in a compact configuration as shown in FIG. 6 such that the connector includes two or more layers of coils. For example, elongated connector 640 includes a first layer of coils 654 and a second layer of coils 656 that is disposed around the first layer of coils. Although depicted as including two layers of coils, the compact configuration of the elongated connector 640 can include any suitable number of layers of coils.

Although not shown, the device 600 can also include one or more frangible attachment elements disposed between a first portion 650 of the elongated connector 640 and a second portion 652 of the elongated connector. The one or more attachment elements can temporarily connect the first portion 650 to the second portion 652 such that the elongated connector is in the compact configuration. The first portion 650 can be temporarily connected to one or more portions of the elongated connector. For example, the first portion 650 can be temporarily connected to the second portion 652 and one or more additional portions of the elongated connector 640. Further, the elongated connector is adapted to be disposed in an elongated configuration when the one or more attachment elements are broken.

The compact configuration of the device 600 can be formed such that the first hearing protector 620 is adjacent the second hearing protector 630 as shown in FIG. 9. Such configuration may allow a user to more easily grasp ends or portions of the connector 640 and apply a separation force to the elongated connector by moving the two portions 650, 652 away from each other such that the portions are disconnected.

Figure 7:
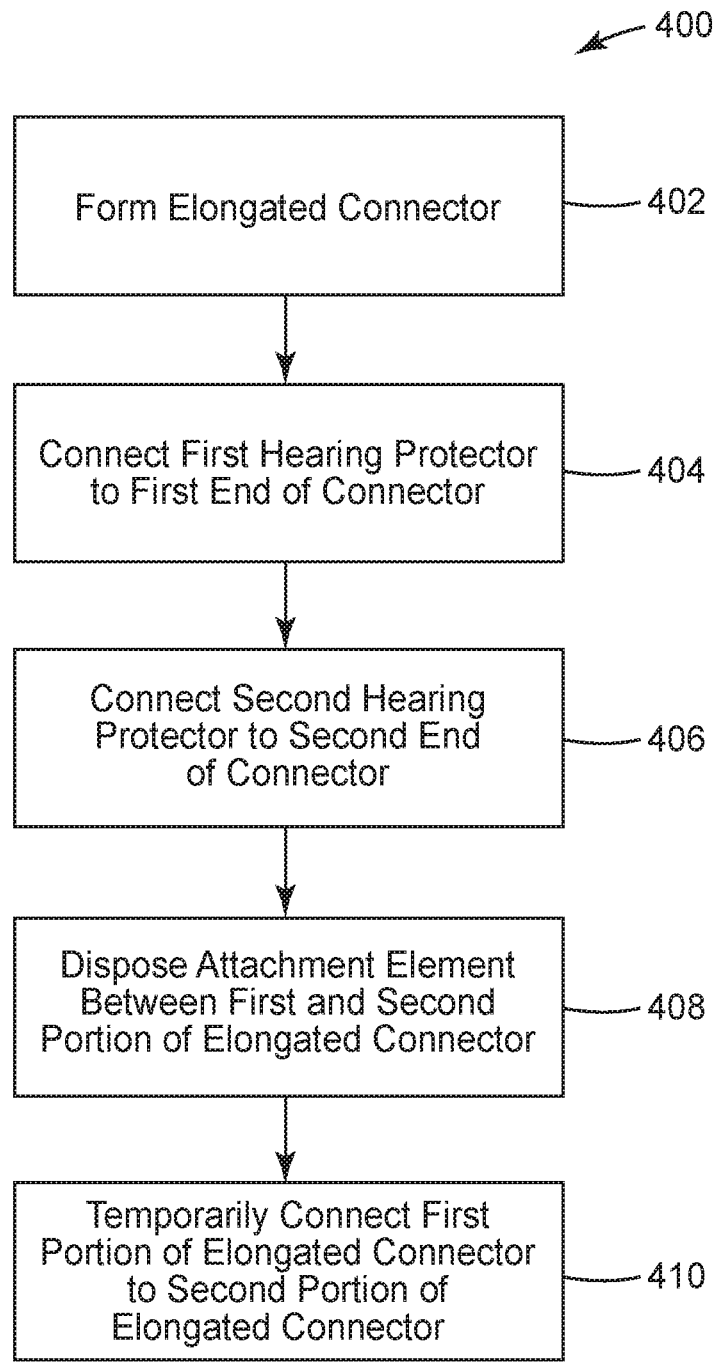
FIG. 7 is a flowchart of one method of forming a hearing protection device.

The various embodiments of hearing protection devices described herein can be manufactured using any suitable technique or combination of techniques. For example, FIG. 7 is a flowchart of one embodiment of a method 400 of forming a hearing protection device 10. Although the method 400 will be described in reference to hearing protection device 10 of FIGS. 1-3, such method can be utilized to form any suitable hearing protection device. The method 400 includes forming the elongated connector 40 at 402. Any suitable technique or combination of techniques can be utilized to form the elongated connector, e.g., extrusion, injection molding, hot stamping, compression molding, mechanical assembling, punching, ultrasonic welding, 3D printing, and combinations thereof. The first hearing protector 20 can be connected to the first end 42 of the elongated connector 40 at 404. Any suitable technique or combination techniques can be utilized to connect the first hearing protector 20 to the first end 42 of the connector 40. In one or more embodiments, one or both of the first and second hearing protectors 20, 30 can be connected to the elongated connector 40 after portions of the elongated connector have been connected. The second hearing protector 30 can be connected to the second end 44 of the connector 40 at 406 using any suitable technique or combination of techniques.

At 408 the attachment element 70 can be disposed between the first portion 50 of the elongated connector 40 and the second portion 52 of the elongated connector using any suitable technique or combination of techniques. At 410, the first portion 50 of the connector 40 can be connected to the second portion 52 of the connector using any suitable technique or combination of techniques. In one or more embodiments, the attachment element 70 can be formed between the first and second portions 50, 52. Such attachment element 70 can be formed when the elongated connector 40 is molded. In other words, the attachment element 70 can be molded along with the elongated connector 40. In one or more embodiments, the attachment element 70 can be connected to the first and second portions 50, 52 using any suitable technique or combination of techniques.

To utilize the hearing protection device 10, the user can grasp two portions of the elongated connector 40 and apply a separation force to the elongated connector by moving the two portions in a direction away from each other such that the temporarily connected portions are disconnected by breaking or separating one or more of the attachment elements (e.g., first attachment element 70). For example, in one or more embodiments, the user can grasp the first and second hearing protectors 20, 30 and apply a separation force to the elongated connector 40 by pulling the first and second hearing protectors apart from each other, thereby breaking the attachment elements (e.g., first attachment element 70) and manipulating the elongated connector into the elongated configuration (FIG. 2).

Figure 8:
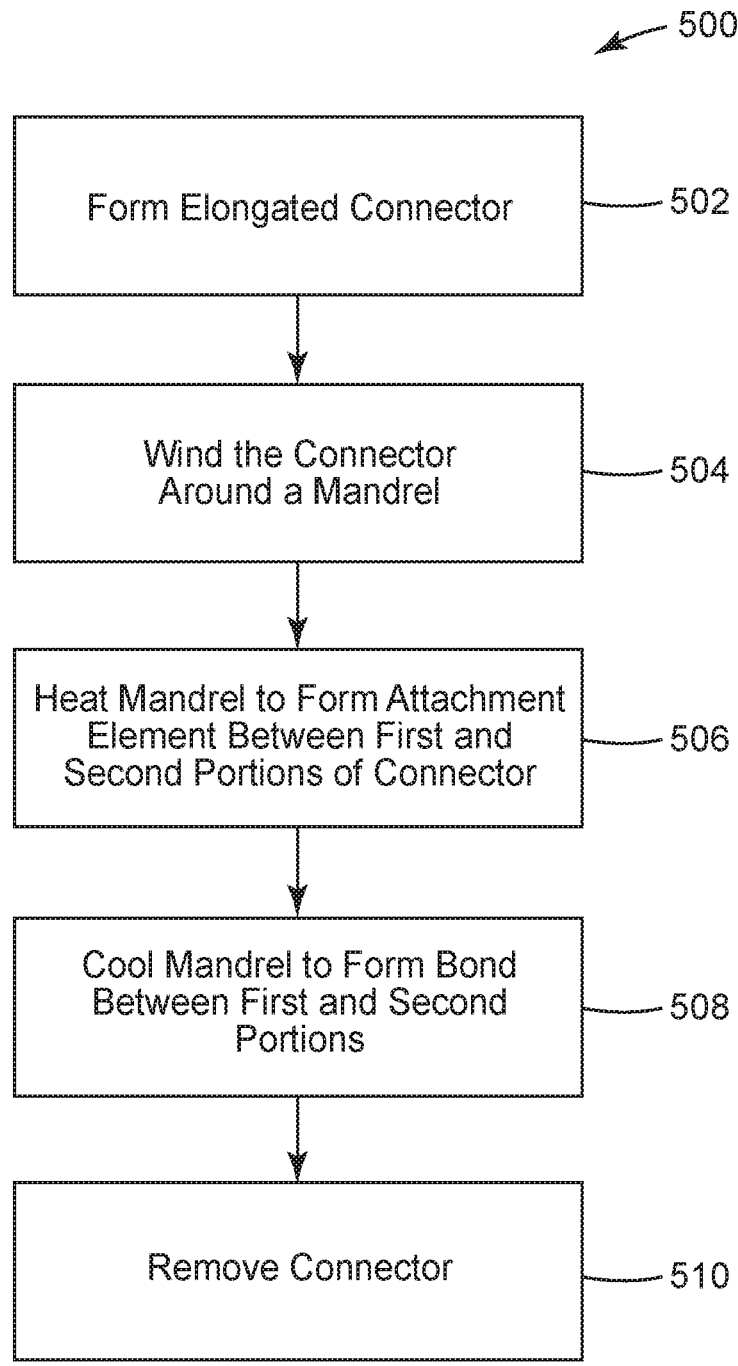
FIG. 8 is a flowchart of a method of temporarily connecting a first portion of an elongated connector of a hearing protection device to a second portion of the elongated connector.

As mentioned herein, any suitable technique or combination of techniques can be utilized to connect two or more portions of the connector 40 together. For example, FIG. 8 is a flowchart of one embodiment of a method of forming an elongated connector into a compact configuration that includes a three-dimensional (e.g., cylindrical) coiled shape as shown in FIG. 5. At 502, the elongated connector 240 can be formed using any suitable technique or combination of techniques. At 504, the connector is wound around a mandrel or rod to form one or more loops 248 in the elongated connector such that the first portion 250 of the connector is in contact with the second portion 252 of the connector. The mandrel can be any suitable mandrel or heating element, e.g., a collapsible rod can be utilized to facilitate demolding of the connector 250 after the coiled configuration has been formed. Further, the mandrel or rod can have any suitable cross-sectional shape, e.g., triangular, rectilinear, ovular, etc. Such cross-sectional shapes can provide different cross-sectional shapes of compact configurations of the elongated connector 240.

The elongated connector 240 can be wound around the mandrel using any suitable technique or combination of techniques. For example, in one or more embodiments, the elongated connector 240 can be extruded onto the mandrel to form the one or more loops 248 in the elongated connector around the mandrel such that the first portion 250 is in contact with the second portion 252. One or more attachment elements can be formed between the first and second portions 250, 252 by heating the rod to a selected temperature such that the first and second portions become tacky at 506. In one or more embodiments, the rod can be heated such that the first and second portions 250, 252 become temporarily connected through one or more attachment elements that are formed using the material of the elongated connector. The rod can then be cooled at 508 such that the elongated connector 240 is also cooled to form a bond (i.e., the attachment element) between the first and second portions 250, 252. The coiled connector 40 can be singulated following attachment of portions of the connector to provide two or more elongated connectors that are in the compact configuration. At 510, the connector 240 can be removed from the rod using any suitable technique or combination of techniques.

Further, for example, any suitable technique or combination of techniques can be utilized to form an elongated connector into a two-dimensional compact configuration, e.g., elongated connector 40 of FIGS. 1 and 3, elongated connector 140 of FIG. 4, and elongated connector 340 of FIG. 6. In reference to elongated connector 40 of FIGS. 1-3, the elongated connector can be disposed in a mold or between two heating platens such that the first portion 50 of the connector is in contact with the second portion 52 of the connector. In one or more embodiments, the connector can be formed prior to being placed in the mold. In one or more embodiments, one or more particulates or solid materials can be placed in the mold to form the connector 40 within the mold. Further, in one or more embodiments, the mold can include injection portions such that molten material can be injected into the mold to form the connector 40. The mold can be closed and heated. While heating, the mold can be compressed such that the first and second portions 50, 52 of the connector 40 are compressed and become tacky. The mold can then be cooled such that the contacting regions of the first and second portions 50, 52 form a bond to provide the attachment element 70 between the first and second portions and any additional attachment elements between additional portions of the connector. Once cooled, the mold can be opened and the connector 40 can be removed.

All references and publications cited herein are expressly incorporated herein by reference in their entirety into this disclosure, except to the extent that they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hearing protection device, comprising:
a first hearing protector;
a second hearing protector;
an elongated connector comprising a first end that is connected to the first hearing protector and a second end that is connected to the second hearing protector; and
a plurality of frangible attachment elements disposed alternatively with a plurality of portions of the elongated connector, wherein each of the frangible attachment elements temporarily connects one portion to the other portion of two adjacent portions of the elongate connector such that the elongated connector is in a compact configuration, wherein the elongated connector is adapted to be disposed in an elongated configuration when any one of the frangible attachment elements is broken, and wherein the plurality of frangible attachment elements are molded integrally with the plurality of portions of the elongated connector.

2. The device of claim 1, wherein the compact configuration of the elongated connector comprises a coiled shape.

3. The device of claim 2, wherein the coiled shape comprises a two- dimensional coiled shape.

4. The device of claim 2, wherein the coiled shape comprises a three- dimensional coiled shape.

5. The device of claim 1, wherein the compact configuration of the elongated member comprises a serpentine shape.

6. The device of claim 1, wherein the elongated connector is adapted such that the frangible attachment element can be broken by moving the first end of the elongated connector in a direction away from the second end.

7. The device of claim 1, wherein the frangible attachment element can be broken by a separation force that is less than a tensile strength of the elongated connector.

8. The device of claim 1, wherein the first and second hearing protectors comprise earplugs.

9. The device of claim 8, wherein each of the first and second hearing protectors comprises a resilient foam body including first and second ends, wherein the first end is adapted to be inserted into an ear canal of a user and the second end is adapted to be connected to the elongated connector.

10. The device of claim 8, wherein each of the first and second hearing protectors comprises a pre-molded body of a resilient polymeric material.

11. The device of claim 1, wherein the elongated connector comprises a thermoplastic material.

12. The device of claim 1, wherein the elongated connector comprises a first coupler adjacent the first end and a second coupler adjacent the second end, wherein the first and second couplers are adapted to connect the first and second hearing protectors to the connector.

13. The device of claim 1, wherein the frangible attachment element comprises an adhesive.

14. The device of claim 1, wherein the frangible attachment element comprises a land.

15. The device of claim 1, further comprising an additional frangible attachment element disposed between the first portion of the elongated connector and an additional portion of the elongated connector that temporarily connects the first portion to the additional portion, wherein the elongated connector is adapted to be disposed in an elongated configuration when the frangible attachment element and the additional frangible attachment element are broken.

16. A hearing protection system, comprising:
a plurality of hearing protectors;
an elongated connector comprising a first end that is adapted to connect to a first hearing protector of the plurality of hearing protectors and a second end that is adapted to connect to a second hearing protector of the plurality of hearing protectors; and
a plurality of frangible attachment elements disposed alternately with a plurality portions of the elongated connector wherein each of the frangible attachment elements temporarily connects one portion to the other portion of two adjacent portions of the elongated connector such that the elongated connector is in a compact configuration, wherein the elongated connector is adapted to be disposed in an elongated configuration when any of the frangible attachment elements is broken, and wherein the plurality of frangible attachment elements are molded integrally with the plurality of portions of the elongated connnector.

* * * * *